United States Patent
Tremblay

(10) Patent No.: US 10,309,915 B2
(45) Date of Patent: Jun. 4, 2019

(54) OZONE CONCENTRATION ANALYZER AND METHODS USING SAME

(71) Applicant: SUEZ TREATMENT SOLUTIONS CANADA L.P., Calgary (CA)

(72) Inventor: Marco Tremblay, Montreal (CA)

(73) Assignee: SUEZ TREATMENT SOLUTIONS CANADA L.P., Montréal (CA)

( * ) Notice: Subject to any disclaimer, the term of this patent is extended or adjusted under 35 U.S.C. 154(b) by 172 days.

(21) Appl. No.: 15/506,378

(22) PCT Filed: Aug. 21, 2015

(86) PCT No.: PCT/CA2015/050799
§ 371 (c)(1),
(2) Date: Feb. 24, 2017

(87) PCT Pub. No.: WO2016/029302
PCT Pub. Date: Mar. 3, 2016

(65) Prior Publication Data
US 2017/0241927 A1 Aug. 24, 2017

Related U.S. Application Data

(60) Provisional application No. 62/042,532, filed on Aug. 27, 2014.

(51) Int. Cl.
*G01N 25/28* (2006.01)
*G01N 33/00* (2006.01)

(52) U.S. Cl.
CPC ......... *G01N 25/28* (2013.01); *G01N 33/0024* (2013.01); *G01N 33/0039* (2013.01); *Y02A 50/247* (2018.01)

(58) Field of Classification Search
CPC . G01N 25/28; G01N 33/0039; G01N 33/0024
See application file for complete search history.

(56) References Cited

U.S. PATENT DOCUMENTS 2,899,281 A 8/1959 Olmer
3,153,577 A 10/1964 McCully et al.
(Continued)

FOREIGN PATENT DOCUMENTS

CA 2253690 A1 5/2000
CN 203002211 U 6/2013
(Continued)

OTHER PUBLICATIONS

Soni et al., "Catalytic oxidation of CO in presence of ozone over supported palladium catalysts", Indian Journal ofChemistry, vol. 53A, Apr.-May 2014, pp. 484-492.
(Continued)

*Primary Examiner* — Krishnan S Menon
*Assistant Examiner* — Dwan A Gerido
(74) *Attorney, Agent, or Firm* — Norton Rose Fulbright Canada LLP; Alexandre Daoust

(57) ABSTRACT

The method for analyzing an ozone concentration comprising the steps of: providing at least one catalytic chamber having an ozone decomposition path between an inlet portion and an outlet portion thereof; receiving a sample flow of gas containing ozone by the inlet portion of the at least one catalytic chamber and along the ozone decomposition path; decomposing a totality of the ozone of the sample flow of gas into oxygen in an exothermic reaction along the ozone decomposition path of the catalytic chamber; measuring a first temperature value at a first position and measuring a second temperature value at a second position, the first and second positions being associated with the inlet and outlet portions; evaluating the ozone concentration of the sample flow of gas based on the temperature difference between the second temperature value and the first temperature value and calibration data; and generating a signal indicating the evaluated ozone concentration.

16 Claims, 4 Drawing Sheets

(56) References Cited

U.S. PATENT DOCUMENTS

| | | | |
|---|---|---|---|
| 3,464,797 A | 9/1969 | Hagopian | |
| 4,783,317 A | 11/1988 | Kuerzinger et al. | |
| 5,167,927 A | 12/1992 | Karlson | |
| 5,646,729 A | 7/1997 | Koskinen et al. | |
| 5,811,662 A | 9/1998 | Williams et al. | |
| 6,165,633 A | 12/2000 | Negishi | |
| 6,235,207 B1* | 5/2001 | Conrad | C02F 1/78 210/742 |
| 2002/0071798 A1* | 6/2002 | DeCourcy | B01J 3/04 422/211 |
| 2005/0013726 A1* | 1/2005 | Hill | A61L 2/208 422/3 |
| 2011/0201123 A1 | 8/2011 | Watson et al. | |
| 2011/0201124 A1 | 8/2011 | Schork et al. | |

FOREIGN PATENT DOCUMENTS

| | | |
|---|---|---|
| EP | 0543770 B1 | 8/1997 |
| GB | 1498989 | 1/1978 |
| JP | 5502899 U1 | 2/1980 |
| JP | 01152349 A | 6/1989 |
| JP | 0798291 A | 4/1995 |
| JP | 2001343342 A | 12/2001 |
| JP | 2004085300 A | 3/2004 |
| JP | 2004536303 A | 12/2004 |
| JP | 2010276356 A | 12/2010 |

OTHER PUBLICATIONS

Subrahmanyam et al., "Dynamic behavior of activated carbon catalyst during ozone decomposition at room temperature", Applied Catalysis B: Environment 61, 2005, pp. 98-106.

Soni et al., "Catalytic oxidation of carbon monoxide over supported palladium nanoparticles", Applied Nanoscience, Sep. 22, 2014.

Durme et al., "Post-plasma catalytic technology for the removal of toluene from indoor air: Effect of humidity", Applied Catalysis B: Environment 87, Mar. 2009, pp. 78-83.

Batakliev et al., "Ozone decomposition", Interdisciplinary Toxicology, vol. 7, No. 2, 2014, pp. 47-59.

McElroy et al., "Determination of ozone by ultraviolet analysis", A New Method for vol. II, Ambient Air Specific Methods, Quality Assurance Handbook for Air Pollution Measurement Systems, May 1, 1997, pp. 1-47.

"Catalytic bead sensor", Wikipedia, May 11, 2014, pp. 1-2, retrieved from the Internet on Jun. 16, 2014.

"Explosimeter", Wikipedia, Feb. 27, 2013, pp. 1-2, retrieved from the Internet on Jun. 16, 2014.

\* cited by examiner

OZONE CONCENTRATION ANALYZER AND METHODS USING SAME

FIELD

The improvements generally relate to the field of measuring ozone concentration of a gas stream involving a thermo-catalytic effect, and more particularly measuring ozone concentration of industrial grade.

BACKGROUND

One known technique for measuring a concentration of atmospheric grade ozone involved flowing a stream of gas along a chamber and measuring a difference of temperature between a reference temperature value at an upstream position of the chamber using a thermistor and measuring an instantaneous temperature value at a downstream position of the chamber using a catalyst-covered thermistor. As the stream of gas flows along the chamber, the ozone of the stream of gas that comes into contact with the catalyst-covered thermistor can decompose in an exothermic reaction which causes heating of the catalyst-covered thermistor and increasing of the difference of temperature. The evaluation of the concentration of atmospheric grade ozone can depend on various parameters such as gas pressure, flow rate, instantaneous positions of the thermistors within the chamber, etc.

Furthermore, one known technique for measuring a concentration of industrial grade ozone involved dividing a stream of gas into a reference stream which remains unaltered and a measurement stream which entails an exothermal decomposition of ozone into oxygen by the passage through a bed of activated charcoal. To suitably compare the reference stream and the measurement stream, the latters have to exhibit relatively similar temperature and pressure values. However, since the chemical decomposition of the ozone tends to generate an excess of heat within the measurement stream, the latter generally has to be cooled down to the temperature of the reference stream using iced water baths prior to the comparison of their thermal conductivities and estimation of the concentration of ozone in the gas stream. Although suitable for industrial ozone grade, biases were generally introduced due to differing properties of the reference stream and of the measurement stream.

Although the techniques known in the art were satisfactory to a certain degree, there remained room for improvement. For instance, prior art techniques often required compensating for variations of pressure and temperature. In general, there remained room for improvement in terms of simplifying ozone concentration measurement.

SUMMARY

There is provided a method for analyzing a concentration of industrial ozone which provides a stream of gas along an ozone decomposition path of a thermally insulated catalytic chamber comprising a plurality of catalytic pellets. The passage of the stream of gas across the plurality of catalytic pellets causes an exothermic reaction which decomposes a totality of the ozone of the flow of gas into oxygen along the ozone decomposition path. By measuring a first temperature value at an inlet portion of the catalytic chamber and by measuring a second temperature value at an outlet portion of the catalytic chamber, a concentration of ozone can be evaluated based on the increase of temperature between the outlet portion and the inlet portion of the catalytic chamber. The total decomposition of the ozone inside the catalytic chamber can avoid temperature and pressure compensation and thus reduce complexity related to the evaluation of the temperature and pressure compensation.

In accordance with one aspect, there is provided a method for analyzing an ozone concentration comprising the steps of: providing at least one catalytic chamber having an ozone decomposition path between an inlet portion and an outlet portion thereof; receiving a sample flow of gas containing ozone by the inlet portion of the at least one catalytic chamber and along the ozone decomposition path; decomposing a totality of the ozone of the sample flow of gas into oxygen in an exothermic reaction along the ozone decomposition path of the catalytic chamber; measuring a first temperature value at a first position and measuring a second temperature value at a second position, the first and second positions being associated with the inlet and outlet portions; evaluating the ozone concentration of the sample flow of gas based on the temperature difference between the second temperature value and the first temperature value and calibration data; and generating a signal indicating the evaluated ozone concentration.

In accordance with another aspect, there is provided an ozone concentration analyzer comprising: at least one catalytic chamber having an ozone decomposition path between an inlet portion and an outlet portion thereof, the at least one catalytic chamber receiving a flow of gas containing ozone by the inlet portion and having a plurality of catalytic pellets therein each catalytically reacting with the ozone of the flow of gas to decompose a totality of the ozone into oxygen in an exothermic reaction along the ozone decomposition path of the catalytic chamber, an inlet sensor for measuring a first temperature value at a first position along the ozone decomposition path, an outlet sensor for measuring a second temperature value at a second position along the ozone decomposition path; and an analyzer communicating with the sensors of the at least one catalytic chamber for receiving the first temperature value and the second temperature value therefrom, the analyzer evaluating the concentration of the ozone of the flow of gas based on the temperature difference between the second temperature value and the first temperature value and calibration data.

In accordance with another aspect, there is provided a method for analyzing an ozone concentration comprising the steps of providing a flow of gas along an ozone decomposition path between a first position and a second position, the ozone decomposition path causing an exothermic reaction decomposing a totality of the ozone of the flow of gas into oxygen along the ozone decomposition path; measuring a first temperature value at the first position and measuring a second temperature value at the second position and evaluating the ozone concentration based on the first temperature value and the second temperature value.

In accordance with another aspect, there is provided a catalytic chamber having an ozone decomposition path between an inlet portion and an outlet portion thereof, the catalytic chamber receiving a flow of gas containing ozone by the inlet portion and having a plurality of catalytic pellets therein each catalytically reacting with the ozone of the flow of gas to decompose a totality of the ozone into oxygen in an exothermic reaction along the ozone decomposition path of the catalytic chamber, an inlet sensor for measuring a first temperature value at a first position along the ozone decomposition path, an outlet sensor for measuring a second temperature value at a second position along the ozone decomposition path, the inlet and outlet sensors of catalytic chamber being adapted to communicate with an analyzer for evaluation of the concentration of the ozone of the flow of gas based on the temperature difference between the second temperature value and the first temperature value and calibration data.

Many further features and combinations thereof concerning the present improvements will appear to those skilled in the art following a reading of the instant disclosure.

DESCRIPTION OF THE FIGURES

In the figures.

DETAILED DESCRIPTION

Figure 1:
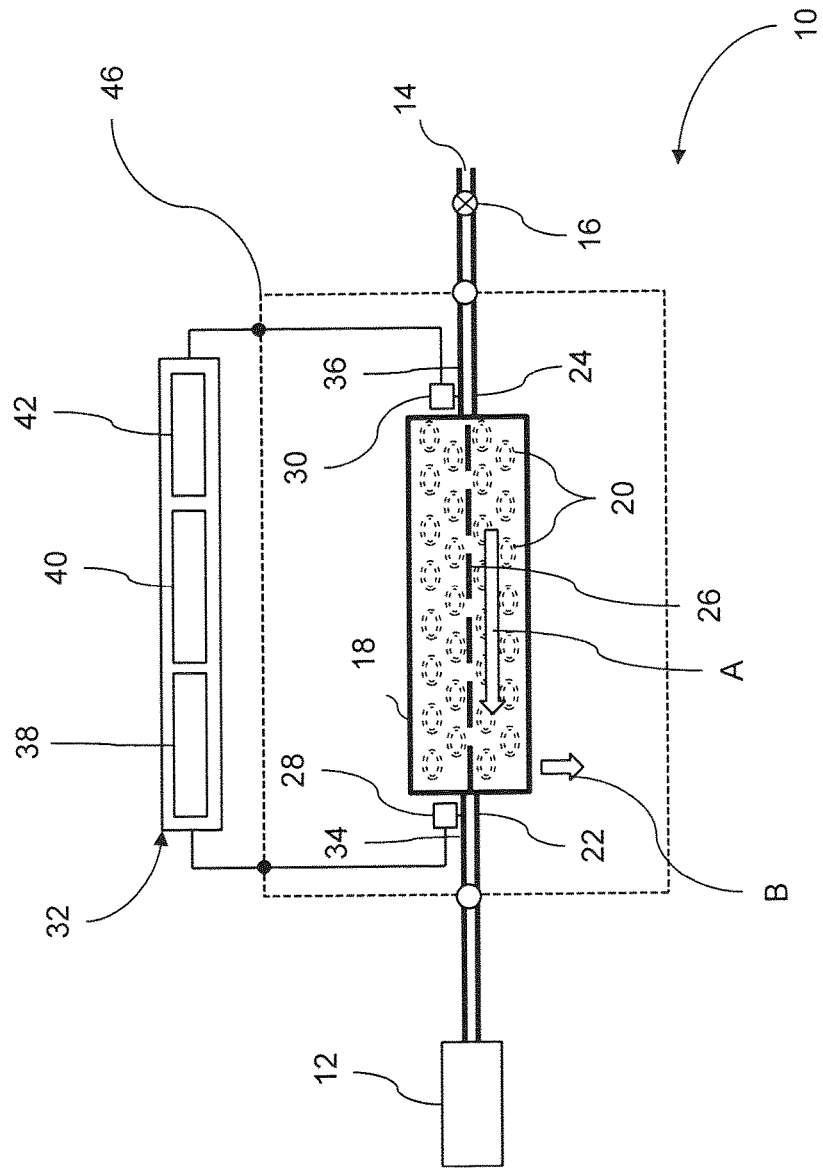
FIG. 1 is a view of schematic view of a first example of an ozone concentration analyzer in accordance with the present invention.

FIG. 1 shows a first example of an ozone concentration analyzer 10 in accordance with the present invention. The ozone concentration analyzer 10 is generally connectable between a gas source 12 and a gas outlet 14, which is opened to the air, for measuring a concentration of ozone of a sample stream of gas supplied by the gas source 12. The measuring method is destructive thus only a sample stream of gas is required. The sample stream of gas is controlled via a valve 16 typically at a position downstream from the ozone concentration analyzer in order to maintain a relatively constant pressure inside the ozone concentration analyzer.

In the embodiment of FIG. 1, the ozone concentration analyzer 10 has a catalytic chamber 18 having a plurality of catalytic pellets 20 therein. Each of these catalytic pellets 20 is adapted to react in an exothermal reaction upon contact with ozone. Many ozone destruction catalysts can be found suitable to this function. For instance, manganese and copper oxides can be suitable as they do not add to the reaction whereas charcoal can be considered unsuitable as it decomposes and is thus another source of heat as it transforms to CO and $CO_2$. Thus, once an ozonized gas contacts the catalytic pellets 20, a totality of the ozone ($O_3$) of the gas can be decomposed in oxygen ($O_2$) and generates heat thereby. Accordingly, a sample stream of gas having a higher concentration of ozone will cause more heat to be generated within the catalytic chamber 18 than a sample stream of gas having a lower concentration of ozone. The amount of heat generated by the exothermal reaction is found to be proportional (as will be described below) with the increase of temperature of a heat carrier, in the case, the oxygen flowing through the catalytic chamber 18. Therefore, the ozone concentration analyzer 10 can measure the heat generated by the ozone in the catalytic chamber 18 and further evaluate the concentration of ozone accordingly. In general industrial applications, ozone concentration can be up to 20 mass percent (% m) of ozone and a small percentage of nitrogen, the decomposition of the ozone can produce a temperature increase of 32.4° C. per 1% per weight of ozone of the sample stream of gas. The increase of temperature is function of the ozone decomposition energy and the heat capacity of oxygen. The concentration of ozone evaluated is independent of the performance of the catalytic pellets 20 as long as the totality of the ozone of the sample stream of gas is decomposed and that the thermal losses of the catalytic chamber 18 are minimized.

The catalytic chamber 18 has an inlet portion 22 and an outlet portion 24 located at two different and/or opposite ends thereof which defines an ozone decomposition path 26, in the catalytic chamber 18, along which the sample stream of gas will flow during use of the ozone concentration analyzer 10. It is contemplated that although the catalytic chamber 18 is shown at FIG. 1 to be oriented horizontally, it can oriented vertically as well. When in vertical orientation, the catalytic chamber 18, the catalytic pellets 20 can be compacted at the bottom thereof which can force the gas flow to pass through the catalytic pellets 20 for decomposition thereof. Both the inlet portion 22 and the outlet portion 24 can be respectively probed with an inlet sensor 28 and an outlet sensor 30 for monitoring, with an analyzer 32, a first temperature value of the sample stream of gas flowing in the inlet portion 22 and a second temperature value of the sample stream of gas flowing in the outlet portion 24. In the first example of FIG. 1, the inlet sensor 28 is provided in an inlet conduit 34 of the inlet portion 22 and the outlet sensor 30 is provided in an outlet conduit 36 of the outlet portion 24. Accordingly, the inlet sensor 28 can be spaced from the catalytic chamber 18 along the inlet conduit 34 in order to minimize heating of the inlet sensor 28. Although the sensors 28, 30 are shown to be external to the conduits 34, 36, it is readily understood that the sensors 28, 30 extend within the conduits 34, 36 for measuring the temperature of the sample stream of gas flowing therein. It is noted, however, that the inlet and outlet portions 22, 24 each covers a relatively large area of the catalytic chamber 18, and therefore, the positions of the sensors 28, 30 are not limited restrictively to the inlet and outlet conduits 34, 36.

A concentration of ozone of the sample stream of gas can be evaluated based on the first temperature value and the second temperature value. Moreover, when a bias induced by thermal losses of the catalytic chamber 18 is minimized, a difference of temperature between the second temperature value and the first temperature value can be considered to vary directly proportionally (linearly) with the concentration of ozone. Considering the thermal losses associated with the catalytic chamber 18, one can calibrate the catalytic chamber 18 as a function of its known parameters, e.g. its form, its construction materials, its size, etc. Indeed, the concentration of ozone may vary as a function of the difference of temperature between the first temperature value and the second temperature value. Accordingly, the catalytic chamber 18 is generally provided with calibration data indicative of the calibration between the concentration of ozone and the difference of temperature, and which compensate for the known thermal losses of the catalytic chamber 18.

The thermal losses can include a thermal conduction loss occurring along the plurality of catalytic pellets 20 (see the conduction loss arrow A) when each of the catalytic pellets 20 conduct heat, generated within the catalytic chamber 18, from the outlet portion 24 to the inlet portion 22. When this occurs, the first temperature value is erroneously increased by heat generated by the presence of ozone in the catalytic chamber 18 and thus tend to lower the difference of temperature between the second temperature value and the first temperature value. To prevent the conduction loss occurring along the plurality of catalytic pellets 20, it was found advantageous to provide a catalytic chamber 18 having an elongated shape along the ozone generated path (linear path or curvilinear path, for instance). Indeed, by having a catalytic chamber 18 of an elongated cylindrical shape having a diameter D and a length L and exhibiting a small ratio D/L, the heat may be prevented from being conducted from the outlet portion 24 to the inlet portion 22 of the catalytic chamber 18. Even if the catalytic chamber 18 is preferred when it has an elongated shape such as a rectangular prism or a cylinder, it can have any suitable shape. Accordingly, the ozone decomposition path 26 is not limited to the linear path shown in FIG. 1.

The thermal losses can also include a thermal insulation losses, or wall losses $Q_{wall}$ (see the insulation loss arrow B) occurring from the catalytic chamber 18 to its external environment. The insulation loss can therefore be minimized by thermally insulating the catalytic chamber 18 or by manufacturing it in a thermally insulating material. It should be kept in mind that measuring a concentration of ozone of 10 mass percent may produce an increase of temperature of 324° C. within the catalytic chamber 18. Thus, a catalytic chamber 18 having a poor insulation may be not only lead to inaccurate measurements, it may also be risky for maintenance workers.

Figure 3:
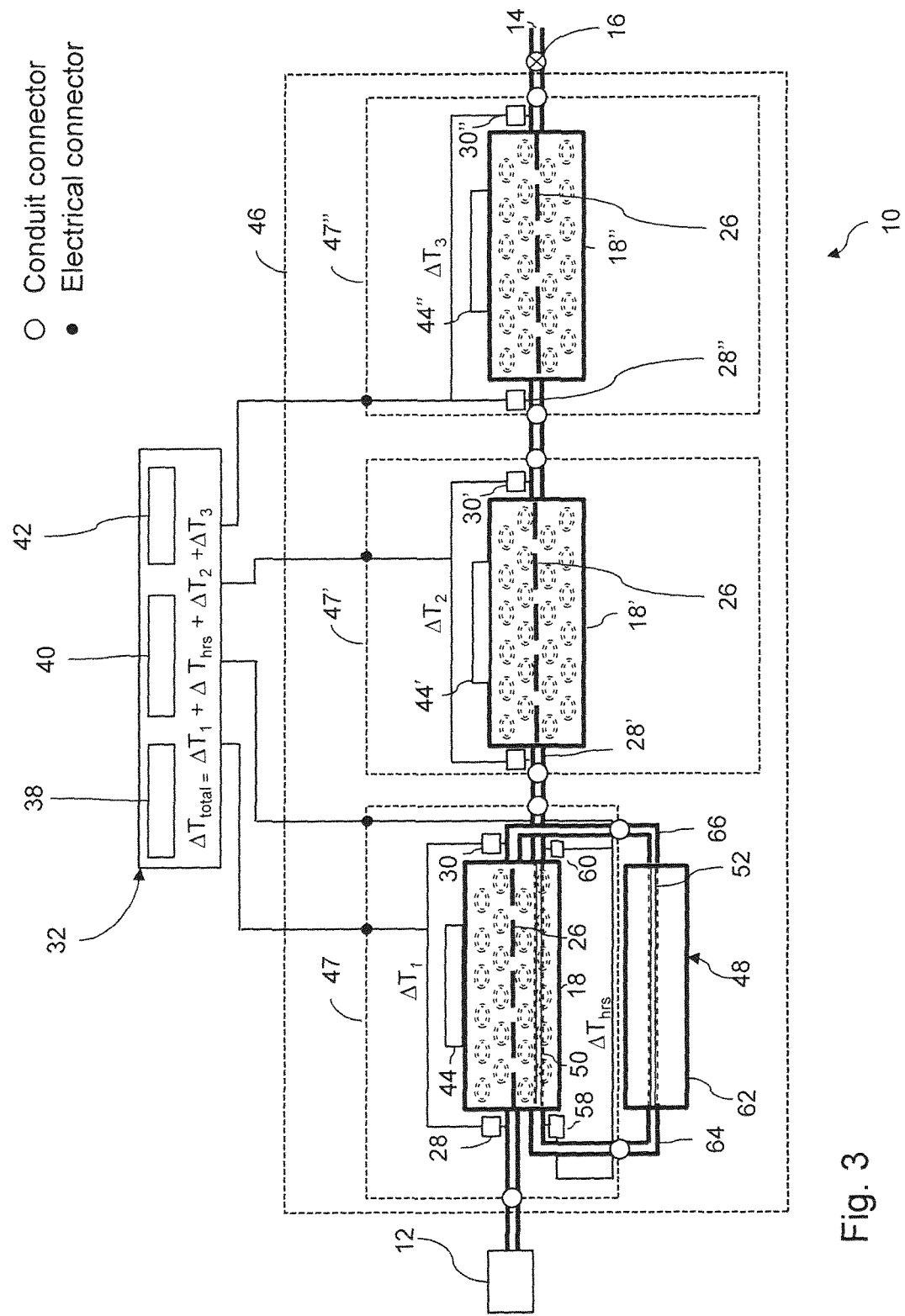
FIG. 3 is a view of schematic view of a third example of an ozone concentration analyzer in accordance with the present invention.

In the embodiment shown in FIG. 1, the analyzer 32 is removably connected to the catalytic chamber 18 via electrical connectors (see black dots). The analyzer 32 The analyzer 32 can be in wireless or in wired communication with the inlet sensor 28 and the outlet sensor 30 for respectively receiving the first temperature value and the second temperature value. The analyzer 32 can have a processor 38, a memory 40 and a display 42 each connected one to the other. It can be preferred to store the calibration data on the memory 40 of the analyzer 32 based on the catalytic chamber 18 thus allowing the analyzer 32 to evaluate the concentration of ozone based on the first and second temperature values, or alternatively to provide a calibration memory 44 (as shown in FIG. 3) directly connected to the catalytic chamber 18 on which the calibration data is stored upon manufacture and calibration. The measured ozone concentration can be displayed on display 42 and/or transmitted on an external device via a suitable serial link or a 4-20 mA current loop.

Although the inlet and outlet sensors 28, 30 can be removably connectable to the catalytic chamber 18, it is noted that the sensors 28,30 can be made integral to the catalytic chamber 18. Accordingly, one can replace a former catalytic chamber of the ozone concentration analyzer with a newer catalytic chamber only by disconnecting the inlet portion 22 from the gas source 12, by disconnecting the outlet portion 24 from the gas outlet 14 (using conduit connectors, see white circles), by disconnecting the inlet and outlet sensors 28, 30 (using the electrical connectors, see black dots) from the analyzer 32 and by connecting the inlet portion 22, the outlet portion 24 and the inlet and outlet sensors 28, 30 of the newer catalytic chamber into their respective place. For ease of use and ease of manufacture, the catalytic chamber 18 can be mounted on a printed circuit board (PCB) 46 incorporating the inlet sensor 28 and the outlet sensor 30 respectively in the inlet portion 22 and the outlet portion 24 of the catalytic chamber 18.

The equations governing the ozone concentration of the increase of temperature in such an ozone concentration analyzer are described herebelow. Indeed, it is known that the exothermal reaction of the decomposition and/or destruction of ozone is given by:

$$3O_2 \leftrightarrow 2O_3 + \Delta Q \text{ at 1 atm} \tag{1}$$

As the molar energy of the ozone is known to be 143 kJ/mol and the molar mass of ozone is known to be 48 g/mol, the specific ozone decomposition energy is 2.98 kJ/g. In other words, for each gram of ozone decompose in the catalytic chamber 18, 2.98 kJ of energy is generated in the form of heat in the catalytic chamber 18. Of this generated energy, some of it will be absorbed and carried out of the catalytic chamber 18 by a heat carrier, i.e. the oxygen, and some of it will be lost due to thermal losses. As the heat is removed from the catalytic chamber 18 via the heated oxygen, more ozone enters the catalytic chamber thus generating more heat. The net change of energy $\Delta Q_{net}$ in the catalytic chamber 18 is energy produced by the decomposition of ozone $Q_{ozone}$ minus the energy carried away by the heated oxygen $Q_{removed}$ and the thermal losses $Q_{losses}$:

$$\Delta Q_{net} = Q_{ozone} - Q_{removed} - Q_{losses}. \tag{2}$$

When the thermal losses are minimized, $Q_{losses}$ tends to zero and thus can be neglected. In the steady-state, i.e. $\Delta Q_{net}=0$, one may obtain:

$$Q_{ozone} = Q_{removed}. \tag{3}$$

It is worth nothing that among the neglected thermal losses, one may find the energy lost through the walls of the catalytic chamber 18 which can be calculated using the relation:

$$Q_{wall} = \frac{T_{inside} - T_{outside}}{R_{wall}}; \tag{4}$$

where $Q_{wall}$ is the heat lost through the walls, $T_{inside}$ is the average temperature inside the catalytic chamber 18, $T_{outside}$ is the average temperature outside the catalytic chamber 18 and $R_{wall}$ is the thermal resistance of the material forming the walls of the catalytic chamber 18. Another thermal loss can be the heat absorbed by the catalytic pellets 20 $Q_{pellets}$, which impact on the net change of energy will be discussed below. Other thermal losses include an ozone loss $Q_{ozone}$ which tends to zero when the totality of the ozone of the sample stream of gas is decomposed into oxygen, a pressure change loss $Q_p$, a flow rate change loss $Q_v$ and radiant heat losses $Q_r$. It is noted that when the thermal losses are minimized, $Q_{losses}$ is negligible compared to the ozone decomposition energy times the mass flow rate.

Therefore, $Q_{losses}$ may be expressed as:

$$Q_{losses} = Q_{wall} + Q_{pellets} + Q_{ozone} + Q_p + Q_v + Q_r. \tag{5}$$

Returning to equation (3), one may calculate the energy produced by the decomposition of ozone $Q_{ozone}$ using the relation:

$$Q_{ozone} = c \cdot \dot{m}_{gas} \cdot e; \tag{6}$$

where c is the percent of concentration of ozone [g of ozone/100 g of gas], $\dot{m}_{gas}$ is the gas mass flow rate [g/s] of the gas flowing in the catalytic chamber 18 and e is the ozone decomposition energy per mass [kJ/g]. Furthermore, the energy carried away by the heat carrier is given by:

$$Q_{removed} = h_{O2} \cdot \dot{m}_{O2} \cdot \Delta T; \tag{7}$$

where $h_{O2}$ is the specific heat capacity [J/g/° C.] of the heat carrier, i.e. the oxygen, $\dot{m}_{O2}$, is the oxygen mass flow rate [g/s] flowing in the catalytic chamber 18 and $\Delta T$ is the difference of temperature of the heat carrier, i.e. the second temperature value of the outlet sensor minus the first temperature value of the inlet sensor. When solving for the concentration of ozone c using equations (6) and (7), one may find:

$$c = \frac{h_{O2} \cdot \dot{m}_{O2} \cdot \Delta T}{\dot{m}_{gas} \cdot e}. \quad (8)$$

Since the ratio of the oxygen mass flow rate and the gas mass flow rate is approximately equal to the unity, one may simplify equation (8) and obtain:

$$c = \frac{h_{O2} \cdot \Delta T}{e}. \quad (9)$$

Based on equation (9), one can understand that the concentration of ozone can be directly proportional to the difference of temperature $\Delta T$. Indeed, by measuring the difference of temperature in such a system, and my minimizing the thermal losses $Q_{losses}$, a reliable concentration of ozone can be measured. Moreover, by computing the ratio $h_{O2}/e$, using the values given hereabove, one may obtain $h_{O2}/e=0.03$ mass percent of ozone/° C. For instance, by measuring a difference of temperature of 100° C., one may find a concentration of ozone of 3 mass percent by easily multiplying the difference of temperature $\Delta T$ to 0.03 mass percent of ozone/° C. One can also state that the temperature of the heat carrier increases of 32.4° C. per mass percent of ozone, and therefore divide the difference of temperature, let's say 100° C., by 32.4° C. per mass percent of ozone and obtain a concentration of ozone of 3 mass percent.

Now referring to the equation (2), the net change of energy $\Delta Q_{net}$ is non-null in a transient state and null in a steady-state. Generally, the time required to achieve the steady-state is referred to as a time constant. Typically, one can suitably evaluate the equilibrium temperature after three time constants. It is to be noted that the time constant of the system depends at least on the material of the catalytic pellets 20. The thermal mass of the catalytic pellets can influence the time constant of the catalytic chamber 18. For instance, the specific heat capacity of the catalytic pellets can by 0.8 J/g/° C. Due to these considerations, the steady-state can be achieved within a shorter or a longer period of time depending on the material (and its total mass) forming the catalytic pellets 20 and on its total mass. It is noted that the time constant is generally inversely proportional to the mass of the catalytic pellets 20 used in the catalytic chamber 18. Accordingly, one may minimize the mass of the catalytic pellets 20 to achieve a shorter time constant thus enabling a higher time resolution of the measured ozone concentration.

As seen by these equations, each one of the terms of $Q_{losses}$ presented in equation (5) is to be minimized in order for the evaluation of the ozone concentration to be reliable. For instance, placing the valve 16 downstream of the catalytic chamber 18 contribute to minimize the pressure change loss $Q_p$, and the flow rate change loss $Q_v$. Indeed, any other suitable manner which can contribute to minimizing $Q_p$ and $Q_v$, or alternatively equalizing the flow rate at the inlet portion 22 and at the flow rate at the outlet portion 24, may render the approximations made above more reliable.

Example of the Evaluation of the Concentration of Ozone

For instance, if a sample stream of gas is provided in the ozone concentration analyzer, and that the sensors read a first temperature value of 20° C. and a second temperature value of 85° C., the analyzer can determine a difference of temperature of 65° C. Based on the calibration data of the catalytic chamber, this difference of temperature of 65° C. may be indicative of a certain amount of decomposed ozone molecules into oxygen, which, may be indicative of a concentration of ozone of 65° C. times 0.03 mass percent of ozone/° C. to obtain 2 mass percent of ozone. In another example, a difference of temperature of 130° C. may be indicative of 4 mass percent of ozone. The measured concentration of ozone is independent of the flow of the sample stream of gas and the volume of the catalytic chamber 18, however these variables may influence the rate at which the ozone concentration analyzer responds.

Figure 2:
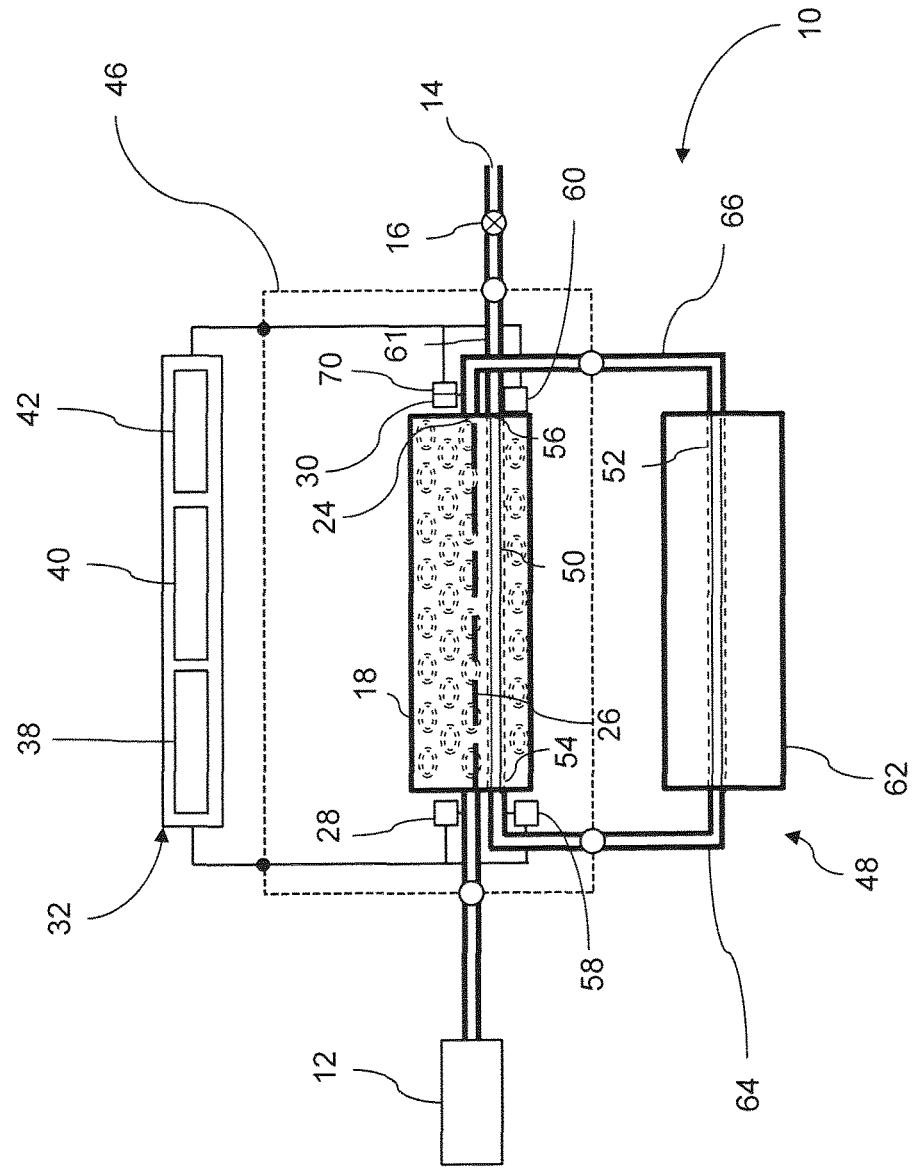
FIG. 2 is a view of schematic view of a second example of an ozone concentration analyzer in accordance with the present invention.

FIG. 2 shows a second example of an ozone concentration analyzer 10 in accordance with the present invention. In this example, the ozone concentration analyzer 10 has a heat removing system 48 which is removably connected to the catalytic chamber 18 for removing heat therefrom using oxygen as heat carrier. In the second example shown in FIG. 2, the heat removing system 48 is adapted to cool the heat carrier (the oxygen) exiting from the catalytic chamber 18 and to reinsert the cooled heat carrier into the catalytic chamber 18 via an internally thermally conducting conduit 50 in order to extract heat therefrom. Since the same heat carrier is used to cool the catalytic chamber 18, the concentration of ozone can be evaluated using straightforward calculations when the thermal losses are minimized.

Specifically, the heat removing system 48 has an external thermally conducting conduit 52 which is connected to the outlet portion 24 of the catalytic chamber 18, and which extends from the catalytic chamber 18 in an insulated manner prior to being connected to the internally thermally conducting conduit 50. The external thermally conducting conduit 52 receives the heat carrier which is then cooled along its passage in the external thermally conducting conduit 52, outside the catalytic chamber 18. When the cooled heat carrier flows back inside the catalytic chamber 18, via the internal thermally conducting conduit 50, it can reabsorb heat and transport it outside the catalytic chamber 18 via a joint conduit 61.

More specifically, the internal thermally conducting conduit 50 can be mounted across the catalytic chamber 18 from a first arbitrary portion 54 to a second arbitrary portion 56. To avoid the dissipated heat to alter the evaluation of the concentration of ozone, a third temperature sensor 58 for measuring a third temperature value at the first arbitrary portion 54 and a fourth temperature sensor 60 for measuring a fourth temperature value at the second arbitrary portion 56 are provided with the heat removing system 48. Accordingly, the concentration of the ozone of the flow of gas can be modified using the third temperature value and the fourth temperature value relative to the calibration data to evaluate the concentration of ozone. To maximize the cooling process of the heated oxygen (the heat carrier), a heat sink 62 can be mounted along the external thermally conducting conduit 52. Moreover, the catalytic chamber 18 may be isolated from the heat sink 62 to avoid the heat removed from the heat removing system 48 to heat the catalytic chamber 18 from the outside. In the example of FIG. 2, the external thermally conducting conduit 52 is connected to the internal thermally conducting conduit 50 via optional insulated conduits 64 and 66. As mentioned above, the difference of temperature obtained can be associated to the concentration of ozone as long as the thermal losses are minimized along the system. Therefore, minimizing leaks along the conduits 64, 66 as well as providing sealed junctions between each of the conduits 50, 52, 64 and 66 is preferable.

Although only one thermally conducting conduit 50 is provided in the embodiments shown in FIG. 2, other embodiments of the heat removing system 48 may have more than one thermally conducting conduits 50 across the catalytic chamber 18 to achieve a higher heat dissipation capacity. To implement the heat removing systems 48, one may use an independent configuration or a loop configuration. In the independent configuration, a given volume of heat carrier may pass only once within the catalytic chamber 18. Indeed, in this configuration, the outlet portion 24 of the catalytic chamber 18 is connected to a plurality of (more than one) heat removing systems 48, independently connected to the catalytic chamber 18 one from another. Each of the plurality of heat removing systems 48 has a corresponding set of conduits 66, 52, 68, 50 and 61 serially connected one to the other. Moreover, the resulting joint conduits 61 can be connected to a manifold (not shown) which combine the joint conduits 61 into a single conduit, upstream from the valve 16. In the loop configuration, a volume of heat carrier may pass multiple times within the catalytic chamber 18. Indeed, in this configuration, the outlet portion 24 of the catalytic chamber 18 is connected to a first pass of the heat removing system 48 having the conduits 66, 52, 68, 50 and 61. A second pass (not shown) of the heat removing system 48 has a secondary insulated conduit, a secondary external thermally conducting conduit, another secondary insulated conduit and a secondary internal thermally conducting conduit respectively serially connected to the joint conduit 61, therefore causing the heat carrier to pass a first time in the catalytic chamber via the internal thermally conducting conduit 50 and to pass again a second time via the secondary internal thermally conducting conduit, and so on if more than two internal thermally conducting conduits are used. It is noted that in both the independent configuration and the loop configuration, each internal thermally conducting conduit may require corresponding temperature sensors to evaluate the cooling with each of the pass of the heat removing system 48, but it may be possible to balance the cooling of each pass to obtain consistent results thus avoiding the need for multiple sensors.

Slow changes in dirt accumulation along the external thermally conducting conduit 52, the heat sink 62, wind, or ambient temperature changes do not affect the ozone concentration measurements since the same gas heat carrier is used along the heat removing system 48. Transient events do have an effect on the measurements when their time period is in the range of the time constant of the ozone measurement. One can compensate for these changes by adding the gas temperature from the heat sink through a high pass filter (not shown) with the correct gain and time constant to compensate for the response time of the ozone measurement. Moreover, the heat removing system 48 can include a controlled cooling device (not shown), such as a fan for instance, to modify the sensitivity of the analyzer 32 based on the second temperature value, or any other suitable parameter. By modifying the cooling rate of the controlled cooling device (e.g. increasing/decreasing a rotational speed of the fan's blades), the ozone concentration analyzer 10 can be suited for different scenarios. Indeed, a higher sensitivity can be achieved when the cooling rate of the controlled cooling device is low in order to measure a low concentration of ozone. Alternatively, a lower sensitivity can be achieved when the cooling rate of the controlled cooling device is higher in applications when the concentration of ozone is high and where a lower sensitivity is acceptable.

Since the same gas mass flow is used in each thermally conducting conduit(s) 50, 52 passing through the catalytic chamber 18, one can add the increase of temperature between the fourth and the third temperature sensors 58, 60 to the difference between 28 and 30 to obtain the difference of temperature which is used for obtaining the concentration of ozone.

Furthermore, it is to be noted that the heat removing system 48 should be insulated from the catalytic chamber 18 in order for the cooling of the catalytic chamber 18 to be performed solely by the heat carrier, i.e. the oxygen. Indeed, if the heat removing system 48 is in physical contact with the catalytic chamber 18, the energy lost through the walls of the catalytic chamber 18 $Q_{walls}$ can be increased which will render the approximations inaccurate. To help achieve insulation between the catalytic chamber 18 and the heat removing system 48, the insulated conduits 64 and 66 can be made of an ozone resistant insulator material such as silicones or polytetrafluoroethylene (PTFE), for instance.

Example of the Use of the Heat Removing System

For instance, if a sample stream of gas is provided in the ozone concentration analyzer 10, and that the inlet and outlet sensors 28, 30 read a first temperature value of 20° C. and a second temperature value of 45° C., the third and fourth temperature sensors 58, 60 read a third temperature value of 30° C. and a fourth temperature value of 42° C., the analyzer 32 can determine a difference of temperature of 25° C.+12° C.=37° C. Based on the calibration data of the catalytic chamber 18, this difference of temperature of 37° C. may be indicative a concentration of ozone of 37° C. divided by 32.4° C. per mass percent of ozone to obtain 1.14 mass percent of ozone.

Still in this example, it was found useful to monitor a humidity value at the outlet portion 24 using a humidity sensor 70. Indeed, if the sample stream of gas contains water vapor, the concentration of ozone can be adjusted based on the humidity value. Indeed, the governing equations presented above are more accurate when the heat carrier is the oxygen. In the event where water vapor would also act as a heat carrier along the catalytic chamber 18, the approximations made above may be less valid. However, the calibration data can compensate for the presence of water vapor. This can be explained by the heat capacity of water vapor (2.08 J/g/K) is about twice the heat capacity of the oxygen (0.918 J/g/K) per weight and the water vapor density (0.804 g/L at standard temperature and pressure) is about half the density of oxygen (1.42 g/L) which typically results in a small difference in thermal transport capacity even in a relatively humid sample stream of gas. Indeed, in this situation the water vapor is characterized by a thermal transport capacity of 2.08 J/g/K times 0.804 g/l equals 1.67 J/l/K while the oxygen has a thermal transport capacity of 0.918 J/g/K times 1.42 g/l equals 1.30 J/l/K. In the less typical case where the sample stream of gas contain mostly water vapor, the adjustment can be 22% higher than when the sample stream of gas is exempt of water vapor. In most practical cases involving streams of gas at room temperature, the saturation limits the humidity level to 2-3% per weight (100% RH=15 g of water per kg of air at ambient conditions) producing error of 0.6% of the full scale. It is noted that in high humidity applications, a pre-heater (not shown) may be installed upstream from the catalytic chamber 18 in order to warm up a humid sample stream of gas to avoid condensation of the humid sample stream of gas onto the catalytic pellets 20 which would reduce their decomposition efficiency.

The nitrogen content has little effect on the result since nitrogen and oxygen have similar thermal capacities. When nitrogen is present in large quantity within the sample stream of gas, the result can generally vary as a function of the total mass flow including the nitrogen. If the fraction of nitrogen is known, one can enter it manually in the analyzer to adjust the result for ozone fraction to oxygen only.

It is noted that although the second example of the ozone concentration analyzer 10 incorporates both the heat removing system 48 and the humidity sensor 70, other examples of the ozone concentration analyzer 10 can incorporate only the heat removing system 48 or the humidity sensor 70. Indeed, low ozone concentration measurements (residual ozone measurements) which can involve the humidity sensor 70 may not need the heat removing system 48 since only a low ozone concentration is involved and thus a low amount of heat is generated during the measurement. To avoid unnecessary costs, the heat removing system 48 and the humidity sensor 70 may be provided, and/or omitted, in accordance with a specific application.

FIG. 3 shows a third example of an ozone concentration analyzer 10 in accordance with the present invention. In this example, the printed circuit board 46 can have three catalytic chambers 18, 18', 18" serially connected one to the other to measure a total temperature difference $\Delta T_{total}$. Each of these catalytic chambers can be mounted on an independent PCB (e.g. see 47, 47', 47") for simple and fast interchangeability of each of the catalytic chambers. In other words, each of the three catalytic chambers shown in FIG. 3 is removably connected to the printed circuit board 46 in a plug and play manner using the conduit connectors (illustrated with the white circles) and the electrical connectors (illustrated with the black dots, for instance. The plug and play of any of the catalytic chambers can be performed in a relatively short period of time, e.g. 15 minutes. The sample stream of gas can be provided by the gas source which can flow along the first catalytic chamber 18, the second catalytic chamber 18' and the third catalytic chamber 18". The first and second temperature values can be monitored for each of the catalytic chambers, using inlet sensors 28, 28' 28" and outlet sensors 30, 30' 30", and used for determining the concentration of ozone of the sample stream of gas. In other words, the inlet and outlet sensors 28, 30 are used to evaluate a first temperature difference $\Delta T_1$, the inlet and outlet sensors 28', 30' are used to evaluate a second temperature difference $\Delta T_2$, and the inlet and outlet sensors 28", 30" are used to evaluate a third temperature difference $\Delta T_3$. Moreover in the example of FIG. 3, the first catalytic chamber 18 is provided with a heat removing system 48 adapted to cool the catalytic chamber using the heated oxygen as heat carrier, as described above. For this purpose, the heat removing system 48 uses the internal conducting conduit 50, the external conducting conduit 52, the insulated conduits 66, 64 as well as the third temperature sensor 58 and the fourth temperature sensor 60. Accordingly, the third and fourth temperature sensors 58, 60 are adapted to evaluate an additional temperature difference $\Delta T_{hrs}$, then the analyzer 32 can evaluate $\Delta T_{total}$ by adding each one of the temperature differences, for instance. In this example, each of the catalytic chambers 18, 18', 18" are provided with a calibration memory shown at 44, 44' and 44". The calibration memories 44, 44', 44" each has a calibration data stored thereon, possibly beforehand, for allowing the analyzer 32 to correctly evaluate the concentration of ozone in a suitable manner based on the properties of each catalytic chamber 18.

Serially connected catalytic chambers 18, 18', 18" allow for detection and compensation of inefficient catalytic chambers. Indeed, if the plurality of catalytic pellets 20 of the first catalytic chamber 18 are saturating and can no longer completely decompose the totality of the ozone into oxygen, the analyzer 32 can detect that the difference between the first temperature value and the second temperature value of the second catalytic chamber 18' is significantly greater than zero, and perhaps also the third catalytic chamber 18". In this situation, the analyzer 32 can display an error message on the display 42 advising a user to change the inefficient catalytic chamber. In other words, measuring an increasing $\Delta T_2$ indicates that the catalytic chamber 18 is inefficient and needs to be replaced. Accordingly, measuring an increasing $\Delta T_3$ indicates that the catalytic chamber 18' is inefficient and needs to be replaced. In one embodiment, the error message initiated by the analyzer 32 can turn to yellow when $\Delta T_2$ increases and later turn to red when $\Delta T_3$ increases.

Moreover, it was found that providing catalytic pellets 20 having a low density (porous material, for instance) can increase the contact surface and therefore allow more of the ozone of the sample stream of gas to be decomposed along the ozone decomposition path 26. A large portion of the sample stream of gas in contact with the plurality of pellets 20 may contribute to better results. The pressure of the sample stream of gas has low influence on the measured concentration of ozone as a higher pressure value tends to increase the amount of ozone decomposed proportionally to the heat removing capacity of the sample stream of gas. Similarly, the flow of the sample stream of gas has a negligible effect as long as the contact time is long enough to ensure the complete decomposition of the ozone.

Since the ozone, and more particularly the industrial grade ozone, can be a strong oxidant, utilizing material resistant to ozone such as ceramic, stainless steel or anodized aluminum is of importance. Moreover, connections between the gas source, the ozone concentration analyzer and the gas outlet, or connection within the ozone concentration analyzer preferably involve ozone resistant gaskets and ozone resistant insulators to prevent premature aging thereof.

Basically, the optimum operation relies on using just enough catalyst pellets to destroy all the ozone in the sample stream of gas but not too much to increase the thermal mass of the chamber and thus slow it down.

Although general industrial applications involve an ozone concentration below 15% m, research applications can reach an ozone concentration up to 100% m. The ozone concentration analyzer 10 can handle any concentration of ozone, using an appropriate heat removing system 48, if required. Indeed, the ozone concentration analyzer 10 can handle higher ozone concentration though it may well require a larger heat removing system 48 to keep the internal temperature within the operating range of the catalyst chamber 18. Indeed, only a 15% ozone concentration can increase the temperature of the catalytic chamber 18 of 487.5° C. Accordingly, the type of heat removing system 48 can be adjusted based on the application. In another embodiment, one may use several pairs of internal and external thermally conducting conduits 50, 52 serially connected one to the other in order to remove as much heat as possible from the catalytic chamber 18. In still another embodiment, the heat removing system 48 is not a parallel flow type like the one shown in FIG. 2, it can be a contra flow type which can enhance the heat removing rate. It is noted that other suitable means can be used to increase the heat removing rate of the heat removing system 48. For example, the thermally conducting conduits 50, 52 can have a serpentine path shape, or any other suitable shape. In another example, the heat removing system 48 can be provided in the form of a double pipe heat exchanger (parallel flow or contra flow), a shell and tube heat exchanger, or any suitable heat exchanging system that may be known in the art.

Figure 4:
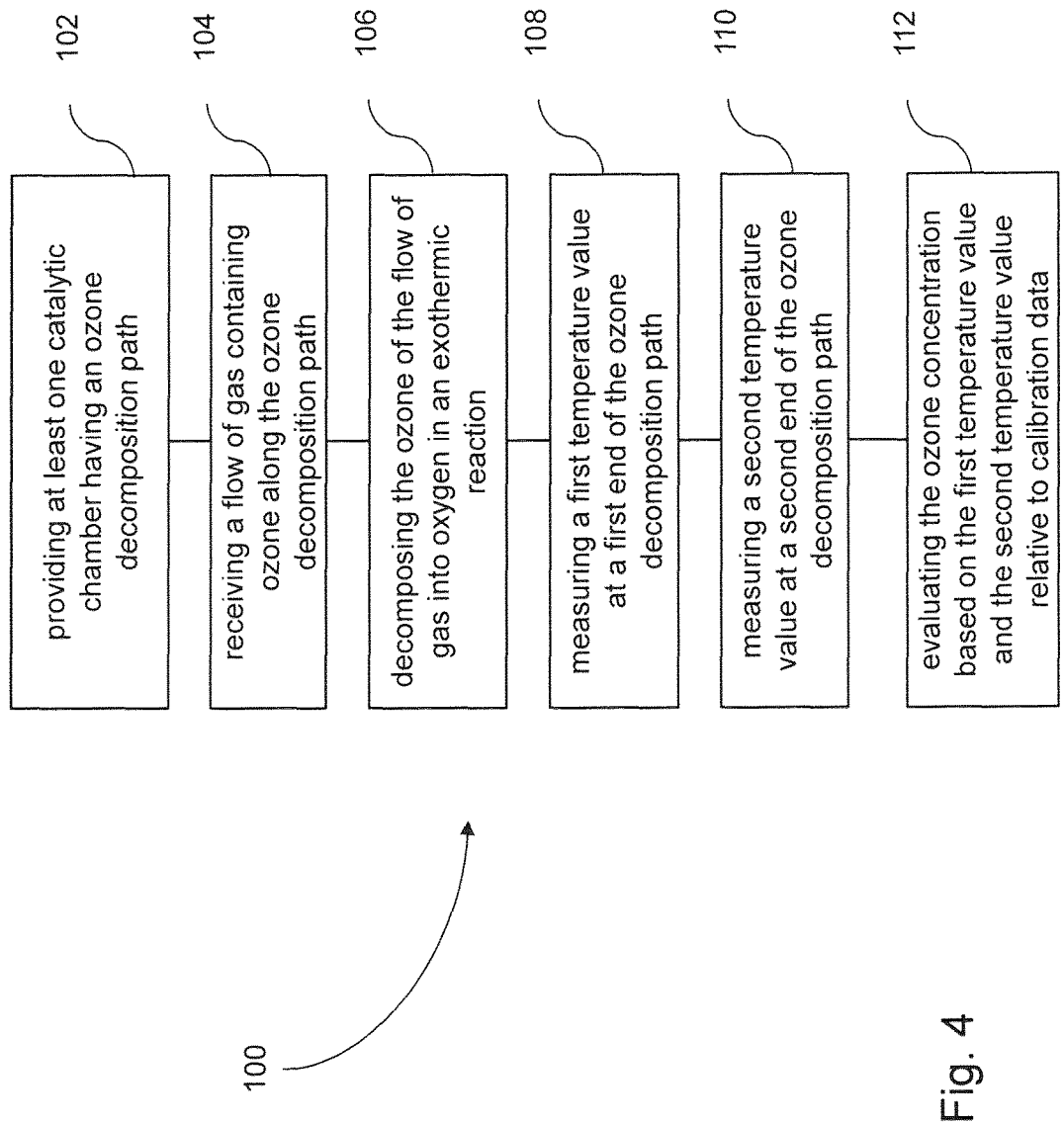
FIG. 4 is a block diagram showing the steps of a method for analyzing an ozone concentration in accordance with the present invention.

FIG. 4 is a block diagram showing the steps of a method 100 for analyzing an ozone concentration in accordance with the present invention. The method generally has a step 102 of providing at least one catalytic chamber 18 having an ozone decomposition path 26 between an inlet portion 22 and an outlet portion 24 thereof, a step 104 of receiving a flow of gas containing ozone by the inlet portion 22 of the at least one catalytic chamber 18 and along the ozone decomposition path 26, a step 106 of decomposing a totality of the ozone of the flow of gas into oxygen in an exothermic reaction along the ozone decomposition path 26 of the catalytic chamber 18; a step 108 of measuring a first temperature value at a first position, a step 110 of measuring a second temperature value at a second position, the first and second positions being associated with the inlet and outlet portions 22, 24; and a step 112 of evaluating the ozone concentration based on the first temperature value and the second temperature value relative to calibration data.

The method 100 can further include a step of measuring a humidity value at the outlet. Afterwards, the step 112 can be based on the measured values relative to calibration data compensating for the humidity value.

Also, the method 100 can further include a step of removing heat from the at least one catalytic chamber 18 (e.g. using a heat removing system as described above) and wherein the step 112 can further comprises evaluating the concentration of the ozone of the flow of gas based on the third temperature value and the fourth temperature value relative to the calibration data. Furthermore, the method 100 can include a step of serially connecting a plurality of catalytic chambers 18 one to the other, wherein said step 112 of evaluating is based on the first and second temperature values each of the plurality of catalytic chambers 18. The method 100 can also include a step of evaluating an decomposition efficiency of each of the plurality of catalytic chambers by comparing the first and second temperature values of each of the plurality of catalytic chambers.

As can be seen therefore, the examples described above and illustrated are intended to be exemplary only. It is noted that the calibration data incorporated in the catalytic chamber can incorporate data related to the constitution of the catalytic pellets therewithin. The calibration data may also be a look-up table in which the analyzer can associate an ozone concentration as a function of a measured temperature difference. Also, the calibration data may correspond to a mathematical operation which is to be performed by the analyzer 32 as a function of a measured temperature difference. Moreover, the calibration data can be a combination of electrical components (particular scheme of ampli-ops, for instance) which can perform the mathematical operation on a measured temperature difference in order to obtain the ozone concentration. The calibration data can further be provided in any other suitable form. Although ozone was discussed extensively hereabove, the concentration of other gas mixture which can be decomposed by a catalyst can be measured with the concentration analyzer 10. The scope is indicated by the appended claims.

What is claimed is:

1. A method for analyzing an ozone concentration comprising the steps of:
   providing at least one catalytic chamber having an ozone decomposition path between an inlet portion and an outlet portion thereof;
   receiving a sample flow of gas containing ozone by the inlet portion of the at least one catalytic chamber and along the ozone decomposition path;
   decomposing a totality of the ozone of the sample flow of gas into oxygen in an exothermic reaction along the ozone decomposition path of the catalytic chamber;
   measuring a first temperature value at a first position and measuring a second temperature value at a second position, the first and second positions being associated with the inlet and outlet portions;
   evaluating the ozone concentration of the sample flow of gas based on the temperature difference between the second temperature value and the first temperature value and calibration data associating reference temperature differences to respective reference ozone concentrations for the at least one catalytic chamber;
   providing the oxygen exiting the outlet portion of the at least one catalytic chamber into an external thermally conducting conduit;
   cooling the oxygen flowing in the external thermally conducting conduit;
   providing the cooled oxygen back in the at least one catalytic chamber using an internal thermally conducting conduit provided across the at least one catalytic chamber from a first arbitrary portion to a second arbitrary portion;
   measuring a third temperature value at the first arbitrary portion and measuring a fourth temperature value at the second arbitrary portion; and
   wherein said evaluating the ozone concentration of the sample flow of gas is further based on the temperature difference between the fourth temperature value and the third temperature value.

2. The method of claim 1, further comprising thermally isolating the external thermally conducting conduit from the at least one catalytic chamber during said steps of providing the oxygen and providing the cooled oxygen.

3. The method of claim 1, wherein said measuring further comprises measuring a humidity value; and wherein said evaluating further comprises evaluating the concentration of the ozone of the flow of gas based on the measured values relative to calibration data compensating for the humidity value.

4. The method of claim 1 further comprising serially connecting a plurality of catalytic chambers one to the other; and wherein said evaluating is based on the first and second temperature values each of the plurality of catalytic chambers.

5. The method of claim 4, wherein said evaluating further comprises evaluating an decomposition efficiency of each of the plurality of catalytic chambers by comparing the first and second temperature values of each of the plurality of catalytic chambers serially connected one to the other.

6. An ozone concentration analyzer comprising:
   at least one catalytic chamber having an ozone decomposition path between an inlet portion and an outlet portion thereof, the at least one catalytic chamber receiving a flow of gas containing ozone by the inlet portion and having a plurality of catalytic pellets therein each catalytically reacting with the ozone of the flow of gas to decompose a totality of the ozone into oxygen in an exothermic reaction along the ozone decomposition path of the catalytic chamber, an inlet sensor for measuring a first temperature value at a first position along the ozone decomposition path, an outlet sensor for measuring a second temperature value at a second position along the ozone decomposition path; and
   an analyzer communicating with the sensors of the at least one catalytic chamber for receiving the first temperature value and the second temperature value therefrom, the analyzer evaluating the concentration of the ozone of the flow of gas based on the temperature difference between the second temperature value and the first temperature value and calibration data associating reference temperature differences to respective reference ozone concentrations for the at least one catalytic chamber; and at least one heat removing system for removing heat from the at least one catalytic chamber using the oxygen heated by the exothermic reaction as heat carrier, each of the at least one heat removing system having:

an external thermally conducting conduit having one end connected to the outlet portion of the at least one catalytic chamber for receiving the oxygen therefrom and another end connected at a first arbitrary position of the at least one catalytic chamber;

an internal therapy conducting conduit provided across the at least one catalytic chamber from the first arbitrary portion to a second arbitrary portion, wherein the heat removing system is adapted to remove heat from the oxygen flowing through the external thermally conducting conduit thus cooling the oxygen and adapted to absorb heat from the at least one catalytic chamber from the cooled oxygen flowing through the internal thermally conducting conduit; and;

a third temperature sensor for measuring a third temperature value at the first arbitrary portion and a fourth temperature sensor for measuring a fourth temperature value at the second arbitrary portion, the analyzer further evaluating the concentration of the ozone of the flow of as based on the temperature difference between the fourth temperature value and the third temperature.

7. The ozone concentration analyzer of claim 6, wherein each of the at least one heat removing system has a first insulated conduit being connected between the outlet portion of the at least one catalytic chamber and the one end of the external thermally conducting conduit and a second insulated conduit being connected between the other end of the external thermally conducting conduit and the first arbitrary position of the at least one catalytic chamber thus thermally insulating the external thermally conducting conduit from the at least one catalytic chamber.

8. The ozone concentration analyzer of claim 6, wherein the at least one catalytic chamber is thermally insulated from the external environment to prevent thermal losses.

9. The ozone concentration analyzer of claim 6, wherein the first position is associated with the inlet portion and the second position is associated with the outlet portion of the at least one catalytic chamber.

10. The ozone concentration analyzer of claim 6, wherein the calibration data comprises at least a listing of reference concentration values as a function of a difference between the second temperature value and the first temperature value for the at least one catalytic chamber having specific dimensions.

11. The ozone concentration analyzer of claim 6, wherein the plurality of catalytic pellets are provided in the form of porous pellets.

12. The ozone concentration analyzer of claim 6, wherein the at least one catalytic chamber further comprises a humidity sensor for measuring a first humidity value at the second position, the analyzer receiving the humidity value and further evaluating the concentration of the ozone of the flow of gas based on the measured values relative to calibration data compensating for the humidity value.

13. The ozone concentration analyzer of claim 6, wherein the external thermally conducting conduit is thermally connected to a cooling device.

14. The ozone concentration analyzer of claim 6, wherein the at least one catalytic chamber has a calibration memory connectable to the analyzer and having thereon data relative to the calibration data thereof.

15. The ozone concentration analyzer of claim 6, wherein the at least one catalytic chamber is made integral to a printed circuit board removably connectable to the analyzer.

16. The ozone concentration analyzer of claim 6, wherein the at least one catalytic chamber is serially connectable to at least one other catalytic chamber.

* * * * *